US011442027B2

(12) United States Patent
Reimer et al.

(10) Patent No.: US 11,442,027 B2
(45) Date of Patent: Sep. 13, 2022

(54) COMPACT MICROWAVE DEVICE FOR MONITORING GRAIN CONDITIONS

(71) Applicant: University of Manitoba, Winnipeg (CA)

(72) Inventors: Alex Reimer, Winnipeg (CA); Yongsheng Gui, Winnipeg (CA); Can-Ming Hu, Winnipeg (CA); Fuji Jian, Winnipeg (CA); Paul Fields, Winnipeg (CA); Digvir Jayas, Winnipeg (CA)

(73) Assignee: University of Manitoba, Winnipeg (CA)

( * ) Notice: Subject to any disclaimer, the term of this patent is extended or adjusted under 35 U.S.C. 154(b) by 502 days.

(21) Appl. No.: 16/548,401

(22) Filed: Aug. 22, 2019

(65) Prior Publication Data

US 2020/0072766 A1 Mar. 5, 2020

Related U.S. Application Data

(60) Provisional application No. 62/725,635, filed on Aug. 31, 2018.

(51) Int. Cl.
*G01N 22/04* (2006.01)
*A23L 7/10* (2016.01)
*G01K 1/024* (2021.01)

(52) U.S. Cl.
CPC .............. *G01N 22/04* (2013.01); *A23L 7/197* (2016.08); *G01K 1/024* (2013.01)

(58) Field of Classification Search
CPC ........ G01N 22/04; G01N 33/02; A23L 7/197; G01K 1/024; A23B 9/00
See application file for complete search history.

(56) References Cited

U.S. PATENT DOCUMENTS

| 2001/0030543 | A1* | 10/2001 | Joshi ................ G01N 33/025 324/643 |
| 2007/0028668 | A1* | 2/2007 | Goto ................... G01N 30/32 73/31.05 |
| 2010/0021611 | A1* | 1/2010 | Yates ................... B02C 19/005 426/555 |
| 2010/0088039 | A1* | 4/2010 | Yang ..................... C07K 1/14 702/23 |
| 2011/0223620 | A1* | 9/2011 | Koyama ............... G01N 5/02 435/7.31 |
| 2017/0303791 | A1* | 10/2017 | Vermeulen ......... A46B 15/0036 |

* cited by examiner

*Primary Examiner* — Christopher P McAndrew
*Assistant Examiner* — Zannatul Ferdous
(74) *Attorney, Agent, or Firm* — Kyle R. Scatterthwaite; Ryan W. Dupuis; Ade & Company Inc.

(57) ABSTRACT

Novel microwave devices capable of monitoring pest activity or moisture content in grain. A planar active microwave resonator with a regenerative element is placed in proximity to the grain to be tested, for example by immersion within in a bulk grain store to monitor moisture levels or pest activity therein, mounting within a sample container to monitor moisture levels or pest activity in a smaller volume of grain sampled from a grain store or shipment, or exposure to individual sample kernels for detecting internal pests therein.

21 Claims, 11 Drawing Sheets

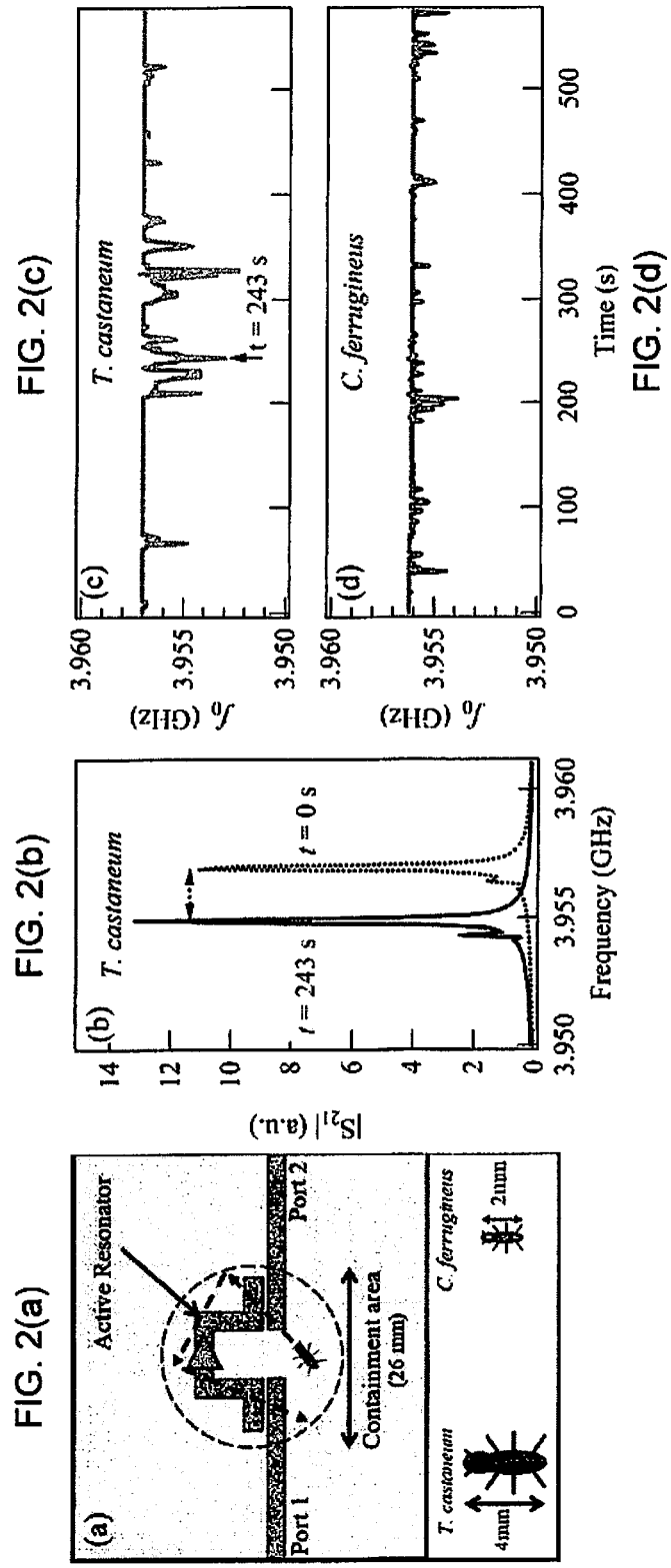

FIG. 3(a)
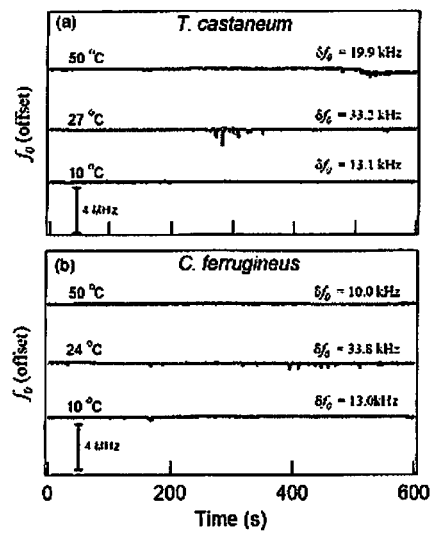
FIG. 3(b)
FIG. 4(a)
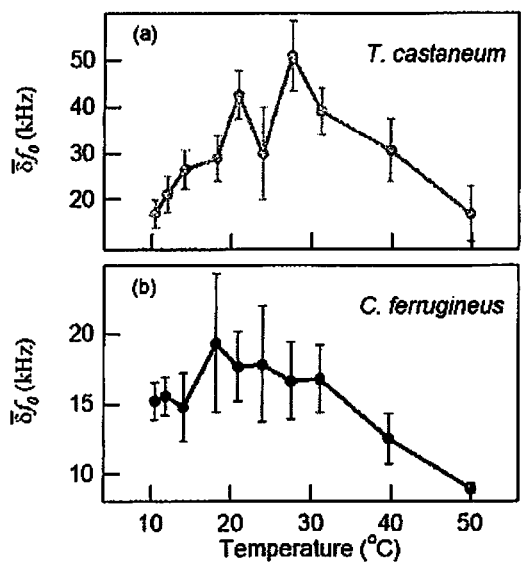
FIG. 4(b)

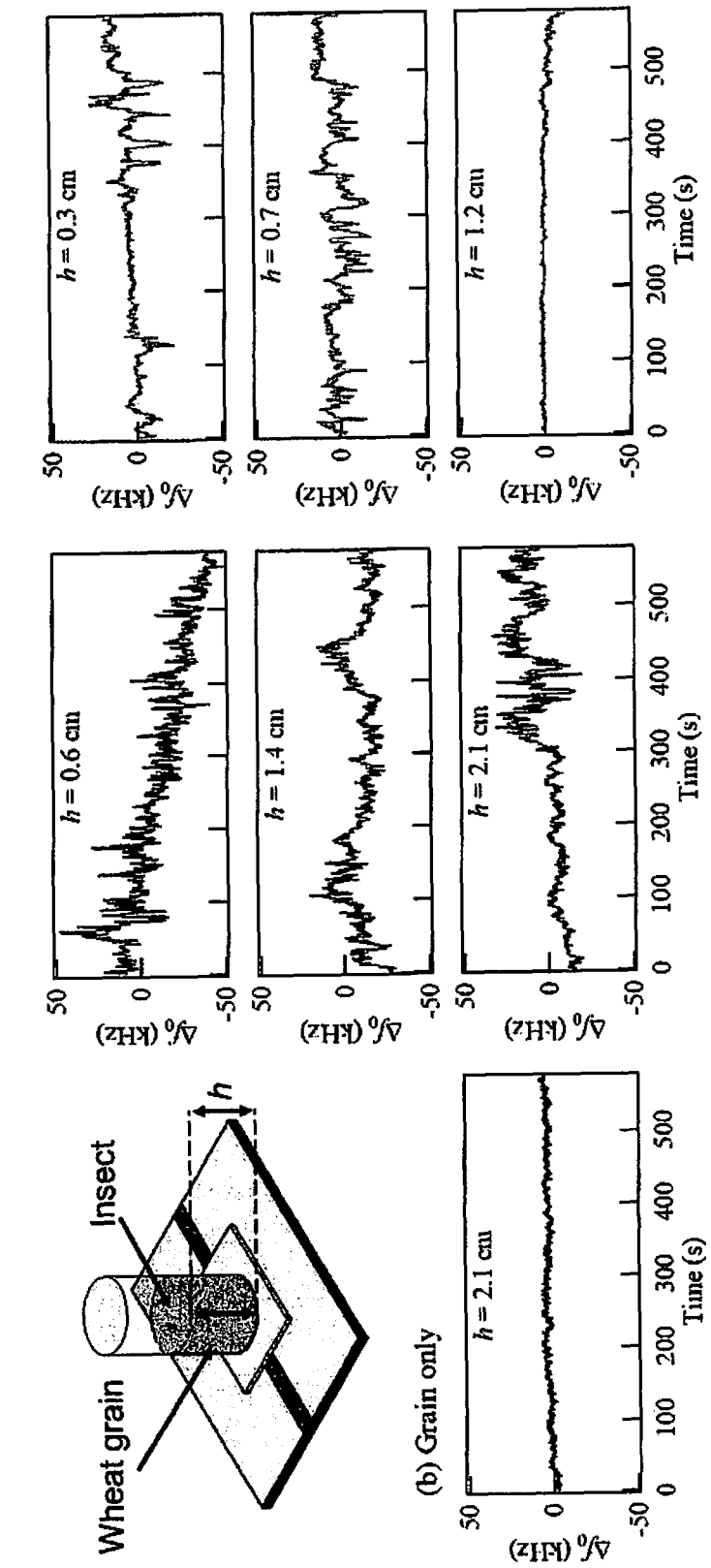

COMPACT MICROWAVE DEVICE FOR MONITORING GRAIN CONDITIONS

CROSS-REFERENCE TO RELATED APPLICATIONS

This application claims benefit under 35 U.S.C. 119(e) of U.S. Provisional Application No. 62/725,635, filed Aug. 31, 2018, the entirety of which is incorporated herein by reference.

FIELD OF THE INVENTION

The present invention relates generally to monitoring of pest activity and moisture in stores or samples of grain, and more particularly to use of resonant cavities to detect the presence of insects in such grain stores or samples.

BACKGROUND

Global climate change and increasing human populations demand a greater and more stable food supply. Two areas of grain store susceptibility include pest infestation and moisture control.

Stored-product insects infest stored grain around the world (Hagstrum et al., 2012). They reduce the quality and quantity of grain, and in several countries there is zero tolerance for insects in stored grain (Hagstrum & Subramanyam, 2006). These insect pests are small, difficult to detect and can quickly cause damage if undetected and not controlled. The current methods (Hagstrum & Subramanyam, 2006) of detecting stored-product insects include manually or mechanically retrieving samples and manually investigating for insects by sieving the sample (Jian et al., 2016), using a Berlese funnel to force internal insects out of wheat kernels (Hagstrum & Subramanyam, 2006), or using traps placed inside stored grain bulks (Jian et al., 2014a). In laboratory settings, more sophisticated techniques such as acoustical methods (Gutierrez et al., 2010), near infra-red (NIR) spectroscopy (Singh et al., 2009), electrical conductance (Pearson & Brabec, 2007; Brabec et al., 2010), and soft x-ray imaging (Karunakaran et al., 2003) have been used to detect insects in bulk grain and inside individual kernels.

Researchers have also turned to microwaves as a tool for insect detection in grain products. Microwaves are especially useful because of their ability to penetrate common, non-conducting materials. Early uses involve radar techniques to detect insects. Microwave radar has shown to be an invaluable tool for studying airborne insect migration (Drake & Reynolds, 2012), and a radar device that can detect termites in walls is commercially available (Termatrac, 2017) and its application to stored product pest detection has been studied (Mankin, 2004). Furthermore, Jian et al. (2014b) developed a technique using microwave heating combined with sieving to extract insects from grain more rapidly than the Berlese funnel method.

In addition to radar technology, microwaves have been used in passive planar cavities for the sensing of materials (Boybay & Ramahi, 2012; Abduljabar et al., 2014) and in biotechnology in applications such as the detection of single cell movement (Ferrier et al., 2009) and the assessment of yeast cell viability (Yang et al., 2010). These devices benefit from low power demand, compact size, on-chip integration, and the ability to perform non-contact sensing. Here, microwave cavities do not rely on the emission of microwave radiation for insect detection, but instead detect the changes in the resonant properties of the cavity when objects (such as moving insects) are present in the vicinity of the cavity. However, passive planar cavities suffer from significant radiative, conductive, and dielectric losses. As a result, the quality factor (Q factor)—which determines the sensitivity and resolution—of passive planar cavity sensors is limited to the order of $10^2$ at room temperature.

Additionally, many species spend their pre-adult stages inside grain kernels. Inside the kernel are laid the eggs, from which larvae will hatch and then excavate the interior to both feed and make space for their growth. They molt, pupate, and eclose while inside the kernel and emerge from it as adults. These internal insects pose a greater challenge to farmers and grain handlers; they can not be easily separated from the grain and more sophisticated measures must be taken to detect and monitor their populations during storage and shipping. Such measures include: soft x-ray radiography near infra-red (NIR) spectroscopy, acoustic detection, electrical conductance and the Berlese Funnel method.

In addition to pest detection, it is important to monitor stored grain moisture content because a product stored at too high a moisture content will deteriorate through infection by fungi and through sprouting. Monitoring is required because it is impossible to completely isolate grain store from external weather effects that may change the moisture content. The moisture content can also change due to internal factors such as the metabolic processes of insects, fungi, and the grain itself.

Accordingly, there remains a need for new and/or improved techniques for monitoring insect activity and moisture content in grain stores.

SUMMARY OF THE INVENTION

According to a first aspect of the invention, there is provided a method of monitoring grain conditions comprising, with an active planar cavity resonator located in proximity with grain to be monitored, monitoring at least one operating characteristic of said active planar cavity resonator for detectable shifts representative of changing conditions within said grain.

According to a second aspect of the invention, there is provided, in combination with grain bin for storing bulk grain, at least one sensor placed within or proximate an interior of the grain bin and comprising an active planar cavity resonator of which an operating characteristic will undergo a detectable shift in frequency in response to changes in conditions in said bulk grain proximate said active planar cavity resonator.

According to a third aspect of the invention, there is provided a grain sample tester comprising a container with an interior space for holding a sample of grain extracted from a larger source of bulk grain, and an active planar cavity resonator situated within or proximate said interior space of the container such that an operating characteristic of the active planar cavity resonator will undergo a detectable shift in response to changes in conditions within said sample of grain.

According to a fourth aspect of the invention, there is provided pest sensor comprising an active planar cavity resonator of which an operating characteristic will undergo a detectable shift in response to changes in conditions proximate said active planar cavity resonator, wherein said active planar cavity resonator occupies a curved plane and is thereby operable to detect conditions in multiple directions faced by said curved plane.

According to a fifth aspect of the invention, there is provided a grain sample tester comprising an active planar cavity resonator and a dielectric support that is affixed to said active planar cavity resonator and comprises a kernel-shaped support surface configured to receive and hold a singular grain kernel thereon in a predetermined position relative to said active planar cavity resonator to enable detection of conditions within said singular grain kernel through monitoring of an operating characteristic of said active planar cavity resonator.

Within any aspect of the invention, the monitored operating characteristic of the resonator may be, for example, the resonator's transmission spectrum, reflection spectrum or output spectrum; or the collector current drawn by the transistor amplifier in the active planar resonator. In the case where the monitored spectrum is that of a transmission or output signal, the frequency being monitored is preferably the peak frequency of the spectrum. In the case where the monitored spectrum is that of a reflection signal, the frequency being monitored is preferably the minimum reflection frequency.

Within any aspect of the invention, confirmation of a shift indicative of said change in conditions may be provided by detection of a sizable shift exceeding a detection threshold, detection of increased fluctuations in said frequency (i.e. increased signal noise), or detection of other notable change in the signal pattern if the environment is already noise prone, even in the absence of any change in moisture content or pest activity.

Within any aspect of the invention, changes in pest-related conditions that trigger a detectable shift and thereby confirm the presence of one or more pests in the grain include (a) change of an occupancy state of a region of a grain store or sample proximate the resonator from a pest-free state absent any pest in said region, to a pest-occupied state in which at least one pest is present in said region; (b) movement of at least one pest from one location to another within said region of the grain store or sample, thus denoting a change in the position of one or more pests within the region; and (c) movement of an internal pest inside a grain kernel residing proximate the resonator.

BRIEF DESCRIPTION OF THE DRAWINGS

Preferred embodiments of the invention will now be described in conjunction with the accompanying drawings in which:

FIG. 2(a) schematically illustrates detection of a single insect by the active planar cavity resonator of the grain sample pest detector of FIG. 1(a) while in the empty (air-filled) state.

FIG. 2(b) illustrates a peak transmission frequency shift resulting from movement from the insect on the surface of the active planar cavity resonator of FIG. 2(a).

FIGS. 2(c) and 2(d) illustrate changes in the peak transmission frequency over time that occur in the presence of two different insect species on the surface of the active planar cavity resonator of FIG. 2(a).

FIG. 3 plots the peak transmission frequency over time for three different temperature conditions in the empty (air-filled) grain sample pest detector of FIG. 1(a) for the two different insect species.

FIG. 4 illustrates the measured activity of both insect species by the grain sample pest detector of FIG. 1(a) at different temperature levels.

FIG. 5(a) illustrates the grain-filled state of a grain sample pest detector of the type shown in FIG. 1(a).

FIG. 5(b) plots the peak transmission frequency over time from the grain sample pest detector of FIG. 5(a) in the absence of any insect.

FIG. 5(c) plots the peak transmission frequency over time from the grain sample pest detector of FIG. 5(a) in the presence of one species of insect at different levels of grain fill.

FIG. 5(d) plots the peak transmission frequency over time from the grain sample pest detector of FIG. 5(a) in the presence of another species of insect at different levels of grain fill.

DETAILED DESCRIPTION

With reference to FIGS. 1 to 5, the present disclosure includes embodiments of a novel microwave-based, on-chip sensor for the monitoring of stored product pest insects. In one preferred embodiment, the sensing element of the sensor is a planar active microwave cavity resonator of microstrip construction with a Q factor as high as 21,600 even in lossy environments, which is a factor 900 greater than a conventional passive resonator (Q=24) in the same environment. The high sensitivity of this sensor enables the detection single adult insects; Tribolium castaneum (Herbst) or *Cryptolestes ferrugineus* (Stephens) at different temperatures. Experimental results show that this technique could provide quick insect detection inside grain samples.

Figure 1A:
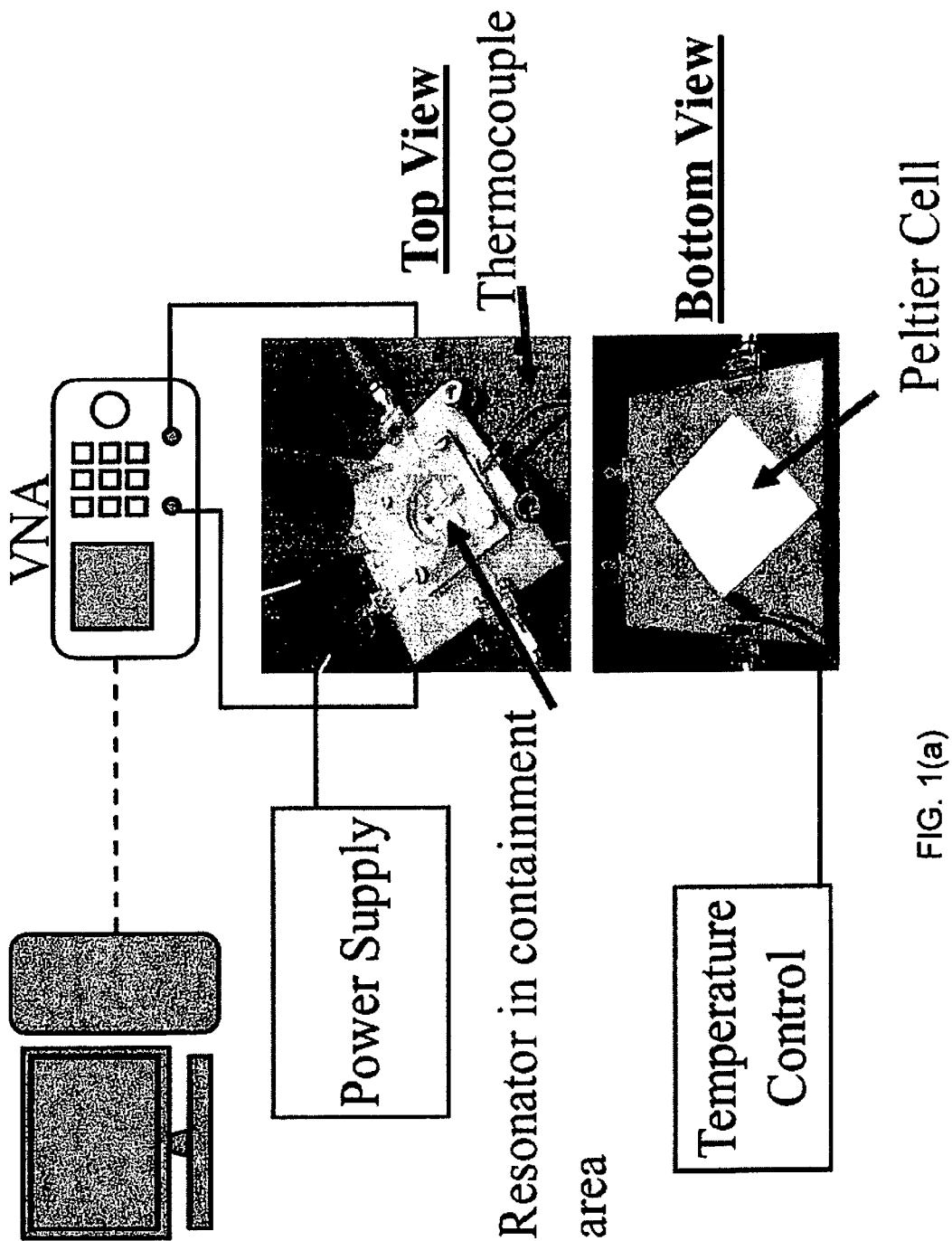
FIG. 1(a) illustrates a grain sample pest detector using active planar cavity resonator according to one embodiment of the present invention.
Figures 1B, 1C:
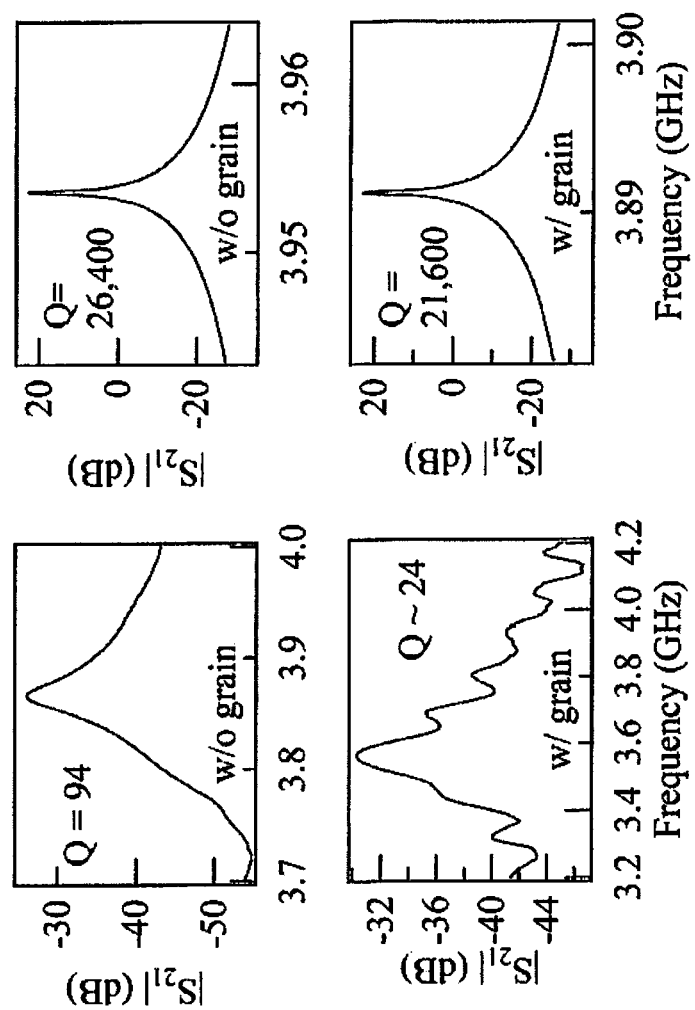
FIG. 1(b) shows graphs of the transmission spectrum of a passive planar cavity resonator of another grain sample pest detector that lacks the regenerative feedback loop of the active planar cavity resonator in the detector of FIG. 1(a).
FIG. 1(c) shows graphs of the transmission spectrum of the active planar cavity resonator of the grain sample pest detector of FIG. 1(a) in empty (i.e. air-loaded) and grain-loaded states.

In order to test the sensor, a grain sample pest detection device of the type shown in FIG. 1(a) was constructed. The device integrates the sensor with a temperature controlled containment structure to confine insects, hold grain samples, and control temperature. FIG. 1(a) illustrates the device setup used in the experimental procedures described below. The circuit board atop which the active planar microwave cavity resonator is defined also defines a container floor of the containment structure. The containment structure also features one or more containment walls standing above the circuit board to delimit a containment space residing directly over the planar active microwave cavity to hold a grain sample and prevent any insect therein from escaping this containment space. In the illustrated example, a singular containment wall was constructed on top of the planar active microwave cavity by fastening a 26-mm diameter and 80-mm height glass cylinder over the surface of the circuit board, thus delimiting a cylindrical containment space over the planar active microwave cavity. To control the temperature within this containment space, a Peltier cell was placed on the side of the board opposite the resonator so as to reside beneath the container floor. The Peltier cell was supplied with a bench top power supply, and the circuit board was secured to a metal heat sink for the Peltier cell. A suitable temperature sensor for measuring the temperature of the containment area was provided in the form of a K-type thermocouple with a Fluke 179 digital multimeter (Everett, Wash., USA).

Two such detectors were constructed for experimental purposes, one with a planar active microwave cavity to demonstrate the principles of the present invention, and one with a planar passive microwave cavity for comparison against the performance of the inventive active cavity detector.

The active and passive resonators for the two test detectors were fabricated using microstrip technology. The planar cavities were designed using Computer Simulation Technology (CST) Studio and constructed in-house by milling a double-sided 35 μm copper clad FR4 substrate for the active resonator, and Rogers DiClad 527 substrate (which has lower dielectric loss than FR-4) (Rogers, 2017) for the passive resonator using a LPKF ProtoMat S103 board milling machine (Garbsen, Germany). The thickness of each substrate was 1.6 mm. The regenerative feedback loop of the resonator was gap-coupled in series to a 50Ω transmission line. An Agilent PNA-L N5230C vector network analyzer (VNA) (Santa Rosa, Calif., USA) was used to measure the frequency response of both the passive and active resonators. Here, the transmission coefficient was measured as $S_{21}$, a complex vector quantity whose magnitude, $|S_{21}|$, is equal to the ratio of the device output to input power wave amplitudes and is commonly expressed on either linear or logarithmic (decibel) scales. Unless specified otherwise, the output power of VNA was set to −20 dBm with −20 dB external attenuation resulting in −40 dBm (0.1 μW) power input to the sensor and an IF bandwidth (the bandwidth of the baseband IF filter internal to the VNA) setting of 1.5 kHz.

The active planar active microwave cavity features first and second microstrip transmission lines on the board, which define first and second connection ports by which the resonator of the inventive sensor is connected to the network analyzer via transmission line cables. The active status of the resonator is due to the inclusion of a regenerative microstrip feedback loop that incorporates a powered amplifier and is gap coupled to the first and second microstrip transmission lines. The cylindrical containment wall encircles the entirety of the microstrip feedback loop, and thus fully encompasses the gap spaces between the ends of the microstrip feedback loop and the two microstrip transmission lines. The microstrip transmission lines reach outwardly beyond the containment wall to the edges of the board for coupling with the transmission line cables that connect to the network analyzer. Other microstrip leads reach from the feedback loop inside the containment wall out to the peripheral edge of the board outside the containment wall to provide the necessary connections to power the amplifier. The planar active microwave cavity thus resides within the confined space of the containment structure at the container floor thereof for direct exposure of the cavity to any grain sample and insect placed within the containment space.

In a first experiment, the sensors of both the active and passive detectors were used to detect insect activity by physical contact of the insect with the planar microwave cavity while the detectors were in an empty state (i.e. air-filled, and absent of any grain). A single adult insect (*T. castaneum* or *C. ferrugineus*) was placed on the surface of the sensor board inside the containment wall and the transmission spectrum of the resonator was recorded by the network analyzer as the insect moved freely on the surface [FIG. 2(a)]. As the insect moved near the resonator microstrips a shift in the transmission peak was observed [FIG. 2(b)]. The greatest shift was observed when the insect was located in one of the two coupling gaps, because signals must transmit through these gaps to enter or exit the feedback loop of the resonator via the microstrip transmission lines. As outlined above, a glass cylinder (26 mm diameter, 80 mm height) was fastened to the sensor board to prevent insect escape from the containment space overlying the resonator [FIG. 1(a)]. The measurement area was shielded with microwave absorber (Cumings Microwave C-RAM LF-77 (Avon, Mass., USA)) to block interfering signals during measurement. The containment space was at a room temperature of approximately 23° C.

To reliably detect the insect, the transmission coefficient $S_{21}$ was recorded for about 10 minutes, corresponding to 960 individual spectrum measurements. The frequency at which maximum transmission occurs, $f_0$, is plotted in FIGS. 2(c) and 2(d). A clear signal was observed for both species, and the magnitude of the peak transmission frequency shifts was found to depend on the size of the insect and its trajectory through the sensitive area of the resonator. Unsurprisingly, the maximum shift of 5 MHz caused by the larger *T. castaneum* was greater than the maximum 2.5 MHz shift caused by *C. ferrugineus* (half the size of *T. castaneum*). The fact that the resonance shifts spanned a range of values and did not simply jump between two states indicated that the transmission peak shifted gradually as the insect moved through the fringing fields of the resonator, whose strength was position-dependent. The maximum shifts correspond to instances when the insect was located in the region where the fringing electric field was strongest, viz. the coupling gaps and the edges of the resonator structure. When the insect was on the edge of the containment space at the containment wall (where the microwave fields were weak), no shifts were apparent. For this measurement, the VNA was configured for a sufficiently large bandwidth to capture the shifts, but also rapid enough to capture insect movement. With these settings, insect movement at the periphery of the glass cylinder containment wall was not apparent. However, shown herein further below, it is possible to detect insect movement without direct between the insect and the sensor surface at the container floor.

Insect activity depends strongly on the temperature of surroundings. *Tribolium castaneum* and *C. ferrugineus* movements are greatly reduced at temperatures below 10° C. (Mahroof et al., 2003) and 8° C. (Arlene-Christina et al., 2014), respectively. Temperatures greater than 45° C. are fatal to both species (Jian et al., 2015). In a second experiment, the sensor's ability to accurately monitor insect activity was demonstrated by performing contact measurements at different temperatures. This experiment was performed by placing an insect in the containment space and allowing it to move freely on the surface of the resonator, as in the first experiment described above. The Peltier cell placed under the board enabled heating and cooling of the resonator [FIG. 1(a)] depending on the polarity of the voltage bias applied to the Peltier cell. The temperature was controlled by adjusting the voltage supplied to the Peltier cell. For each temperature setpoint, the containment area was left to equilibrate—a process taking approximately 10 min—before data were recorded. The transmission spectrum was then recorded over a 10-minute period at an approximate rate of one every second, corresponding to 600 individual measurements.

FIG. 3 displays the peak transmission frequency for both species at selected temperatures spanning the range of temperatures to which insects were exposed. The peak transmission frequency ($f_0$) was recorded over time, and the average absolute peak shift between consecutive spectrum measurements ($\delta f_0$) over the recording period was calculated. This was repeated with 5 individuals of each species to obtain an average measure of the activity. FIG. 4 summarizes the measured activity for all temperatures tested.

*Tribolium castaneum* is about 2 times longer than *C. ferrugineus*, and therefore causes larger shifts, which accounts for its generally greater measured activity. In both species, measured activity was the highest between 20 and 30° C. and decreased outside this range. For both species, measured activity lowered at low temperatures, which is in agreement with the published observations that temperatures below 15 and 17.5° C. inhibit movement in *T. castaneum* (Jian et al., 2005) and *C. ferrugineus* (Jian et al., 2002), respectively. On the other hand, temperatures greater than 40° C. are uncomfortable for both species and caused them to circle the edge of the containment area in an attempt to seek cooler temperatures, explaining the relative decrease in measured activity in this temperature range. Temperatures greater than 50° C. will kill most individuals from both species after 2 hours exposure (Arlene-Christina et al., 2014; Mahroof et al., 2003). Conversely, *C. ferrugineus* prefers temperatures of 30-36.5° C. (Jian et al., 2003) and *T. castaneum* has been observed to move along a temperature gradient to areas of 30° C. (Jian et al., 2005) suggesting a preference for similar temperatures, and so activity measured in this temperature range is markedly lower. Activity was highest from 20 to 30° C. because the temperature is not so low as to inhibit movement, not too comfortable as to discourage movement, and not so high as to encourage escape.

An important practical application of the sensor is the detection of insects in grain bulks. The grain increases the difficulty of insect detection through several factors: 1) insect movement is restricted to the spaces between kernels; 2) the contrast between the dielectric constant of the insect and the grain environment is lower compared to that with an air environment; 3) grain introduces dielectric loss and increases the resonant width, which decreases the sensor's ability to resolve resonance shifts. Of these factors, it was expected that the first and last would be most important. Peak broadening is mitigated by the use of an active resonator, which experiences minimal peak broadening against loss and thus can detect the movement of insects in grain bulk.

As a proof-of-principle, the glass cylinder was partially filled with wheat grain, and a single insect was introduced on the surface of the wheat held inside the 26 mm glass cylinder [FIG. 5]. The transmission spectrum was then recorded every 0.6 seconds for 10 minutes. Over the course of the measurement, the insect was left free to move inside the wheat bulk. The measurement was repeated with grain heights varying from 0.3 cm to 2.1 cm. The measurements were conducted at room temperature and the sensor was shielded from interfering radiation.

Using the case without insects [FIG. 5(b)] as a reference, an indication of activity was seen for *T. castaneum* in FIG. 5 (c) and *C. ferrugineus* in FIG. 5 (d), which had manifested as a signal with seemingly random variations as well as temporary deviations of noticeably greater amplitude. These features might reflect two scales of motion: the random short scale motion of the insect as it searches for paths between individual grains and the longer scale motion as it moves through the bulk. The comparison of results between the active and passive sensors highlighted the necessity of the active resonator to a functional detector. The peak transmission frequency shifts caused by the insect in bulk grain at a distance from the surface of the resonator are dramatically smaller when compared to the peak transmission frequency shifts resulting from direct contact of the insect with the surface of the resonator, decreasing from a few megahertz to at most tens of kilohertz. The greatest variations in $f_0$ seen in FIG. 5 span approximately 50 kHz, corresponding to 28% of the active resonator linewidth, but only 0.03% of the passive resonator linewidth when in grain [FIG. 1(b)]. Considering that most of the variations observed in FIG. 5 are much smaller than 50 kHz and noting the width of the resonance of the passive resonator [FIG. 1(b)], it is concluded that without the active element, a passive microstrip resonator lacks sufficient resolution to be useful for the detection of insects in grain bulk.

Due to its size, *T. castaneum* movement in the bulk grain was restricted and a net displacement from the grain surface where it was introduced was difficult for it to achieve (Jian et al., 2005). This may be apparent in FIGS. 5(c) and 5(d), where temporary changes in $f_0$ are observed at when the insect attempts to move deeper into the grain bulk but fails to find a path deeper into the bulk and so returns to the grain surface and causes $f_0$ to return nearly to its initial value. FIGS. 5(c) and 5(d) also show constant smaller, more rapid variations in $f_0$ not observed in the clean case [FIG. 5(b)]. As the height of the bulk was increased, these variations were diminished by the generally increasing distance of the insect from the resonator.

Similar features were observed in the measurement of *C. ferrugineus* movement in the bulk grain. Since *C. ferrugineus* is significantly smaller than *T. castaneum* and is able to move more freely through the grain bulk, the relatively large changes in $f_0$ were more frequent than those observed with *T. castaneum*. However, the smaller size also reduces overall magnitude of shifts in $f_0$, making it more difficult to detect *C. ferrugineus* at larger distances.

The forgoing results demonstrate that the sensor is capable of detecting and measuring single insect activity in bulk grain. Since the sensor response changes with insect activity, it has the potential for use in monitoring insect population densities. Such monitoring is crucial for farmers and grain handlers who depend on the information to formulate their pest management strategies. One challenge may be the possible ambiguities in sensor signal that results from the dependence of the response on insect size, location, and movement speed.

One way to circumvent this is the use of an array of sensors sunk into grain bulks to increase the reliability of detection. Accordingly, embodiments of the present invention are not limited to the particular grain sample insect detector with its own containment structure for holding a small sample of grain, but rather also extend to in-situ detection systems where a plurality of sensors are placed inside or proximate the interior space of a grain bin at dispersed locations from one another throughout or around the interior space of the grain bin. On the other hand, a single grain sample detector with its own containment structure can alternatively be used in the manner described for the forgoing experiments to quickly test for insects in smaller grain samples pulled from a larger grain bulk, such as that stored within a sensor-lacking grain bin.

It will also be appreciated that though the forgoing description is framed primarily in the context of grain pest detection, other potential applications of the technology also exist. For example, outside of agriculture and food production, the material penetrating ability of the sensor would make it a useful tool for the detection of household pests such as termites, ants, or rodents. Therefore, the particular environment in which a sensor of the present invention is put to use is not limited specifically to a grain storage environment.

There are several measures that can be taken to increase the effectiveness of the sensor. For example, the range of the sensor might be improved by selecting a lower operating frequency, such as between 0.5 GHz and 1 GHz, at which the dielectric loss factor of water is much lower [tan $\delta \approx 0.16$ at 3.25 GHz vs. tan $\delta \approx 0.03$ at 0.58 GHz (at 20° C.) (Franks, 1972)]. Since a significant portion of grain mass is water (10% to 17%) this could allow the microwave fields of the resonator to extend further into the grain bulk.

Figure 13:
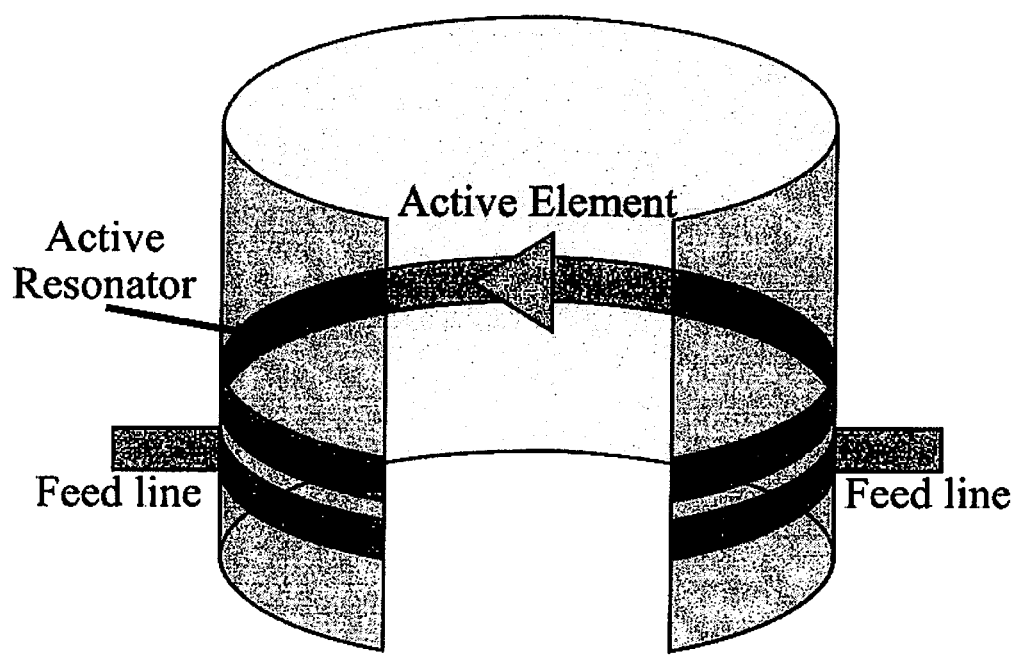
FIG. 13 schematically illustrates an active resonator on a cylindrical substrate.

Another way to increase the performance could be to use a different resonator geometry, for example contouring the planar resonator into a curved plane rather than occupying a conventional flat plane. The sensor can then sense insects in a number of different directions faced by this curved plane of the planar resonator. One example involves wrapping the planar resonator into a cylindrical form so that it may sense insects in a volume completely surrounding the sensor on all sides thereof, rather than on only one side like in the flat-plane embodiment shown in the drawings, where the ground plane of the resonator is located on the other side of the board and terminates the fields guided by the microstrip line. This is illustrated in FIG. 13, a diagram of an active resonator on a cylindrical substrate. Other than its curved shape, the resonator construction is otherwise identical to the resonators shown in FIGS. 2(a) and 5(a). The resonator may be on either the concave interior surface or convex exterior surface of the curved substrate, and the feed lines allow the resonator signal to be extracted for measurement, just like in the planar embodiments.

The experimental results summarized herein demonstrate that the sensor based on a planar microwave active cavity is capable of detecting single adult insect activity through contact as well as in bulk grain. Insect activity is detected by monitoring the transmission spectrum of the cavity, which operates in the 3-4 GHz range, whose peak transmission shifts when insects are nearby. In contrast with a passive cavity, the active cavity has a very narrow transmission spectrum peak, allowing shifts on the order of kHz to be detected. Furthermore, the active cavity is resistant to added dielectric loss in the environment such that it maintains its narrow transmission peak even when placed in grain. Two species of common grain pests were used as subjects in the experimental tests: *T. castaneum* and *C. ferrugineus*. As expected, the larger *T. castaneum* caused greater shifts in the transmission peak than the smaller *C. ferrugineus*. This resulted in a lower measured activity of *C. ferrugineus*, though this does necessarily reflect a lower level of movement. Insects in bulk wheat were also successfully detected at distances up to 2.1 cm with *T. castaneum* and 1 cm with *C. ferrugineus*. The demonstrates approach has potential use as a tool to monitor insect populations in stored grain bulks, such as grain bins, or to non-destructively detect other pests such as termites.

In the experiments described above, the inclusion of the Peltier cell and the thermocouple were for verification purposes so that different degrees of peak transmission frequency shift experienced at different temperature ranges could be compared against known data on the activeness of targeted insect species at such different temperature ranges to test the accuracy and reliability of the sensor. In some commercial iterations, the pest detector may optionally lack a Peltier cell or other temperature control device, and likewise optionally lack a thermocouple or other temperature monitoring device. In other cases, such temperature related equipment may be included so that the reliability and accuracy of the sensor can periodically tested to check whether repair or replacement may be required. In such instances, particularly where the sensor is used in-situ on or inside a grain bin, such testing of the sensor with an intentionally introduced sample of a targeted pest species of known temperature-dependent behaviour is preferably performed only after removing the sensor from its normal in-situ environment to a remote or well-contained testing environment separate therefrom, so that the introduced pest is prevented from accessing the grain bin or other in-situ environment and contaminating same.

The forgoing pest sensor embodiment is used to detect presence of pests moving within a volume of grain in the available space between the individual kernels thereof, whether within a grain store or in a selected sample collected from such a grain store. Such sensors may be referred to herein as external-pest sensors, as the detected pests reside externally of the individual grain kernels.

Turning to FIGS. 6 through 10, another embodiment of the present invention instead concerns an internal-pest sensor for detecting the presence of a pest inside an individual grain kernel. In this embodiment, a new, non-intrusive method of detecting internal insects using microwave sensing technology is proposed. Here, an ultra-high quality (Q) factor planar microwave resonator is employed, whose resonant frequency is extremely sensitive to changes in the environment. The slight movements of internal insects produce measurable shifts in the resonant frequency. The planar kind of microwave resonators consist of conductive 2D structures clad to an insulating board and are fabricated using printed circuit board technology. The electric fields of the resonators extend into the nearby volume and can be used to probe objects without contact; the resonance frequency shifts in accordance with the environment of the resonator. Such resonators have low material costs, simple designs, and are easily manufactured. For these reasons, they are well suited to solve to a broad range of sensing problems. Studies have been done on their application to the measurement of materials, the detection of single-cell movement, and the assessment of yeast cell viability.

The resolution of microwave resonators can be increased by the inclusion of an active element which restores energy lost by the resonator. These "active resonators" exhibit dramatically narrower resonance peaks, with a resolution increased by 2 or 3 orders of magnitude. Such improvements have been used in, for example, the measurement of transient semi-conductor response and the non-contact sensing of liquids. An internal-pest sensor using a planar active resonator can be applied to the problem of detecting internal grain insects. In experimental support of this, it is outlined herein below that each stage of *Sitophilus oryzae* (rice weevil) present inside grain kernels produces a unique response pattern in the internal-pest sensor, and estimations of the detection probability for different observation times is also provided The internal-pest sensor employed in such experimentation and schematically illustrated in FIG. 6(a) consists of a planar microwave resonator through which the transmission of signals is greatest near the resonance frequency (FIG. 6(b)). Microwave frequency electric fields extend into nearby space as they propagate along the feed line and resonator (FIG. 6(a)). Perturbations of the fields, such as the introduction of an object, cause the resonance to shift to a different frequency. With this principle, the movement of insects inside kernels can be detected by probing the kernels with the electric fields and monitoring the transmission of microwaves through the resonator (FIG. 6(a)). Experimental measurements consisted of placing an infested kernel on the internal-pest sensor and monitoring a bandwidth of the transmission spectrum containing the resonance to capture the shifts in the resonance caused by insect movement. A vector network analyzer (VNA) (PNA-L N5230C, Agilent), controlled with custom MATLAB programming, was used to measure the transmission spectrum of the resonator board. The transmission coefficient was measured as $S_{21}$, which is a complex vector quantity whose magnitude, $|S_{21}|$, is equal to the ratio of the voltage wave amplitude at the output to that input to the device.

Figures 6A, 6B:
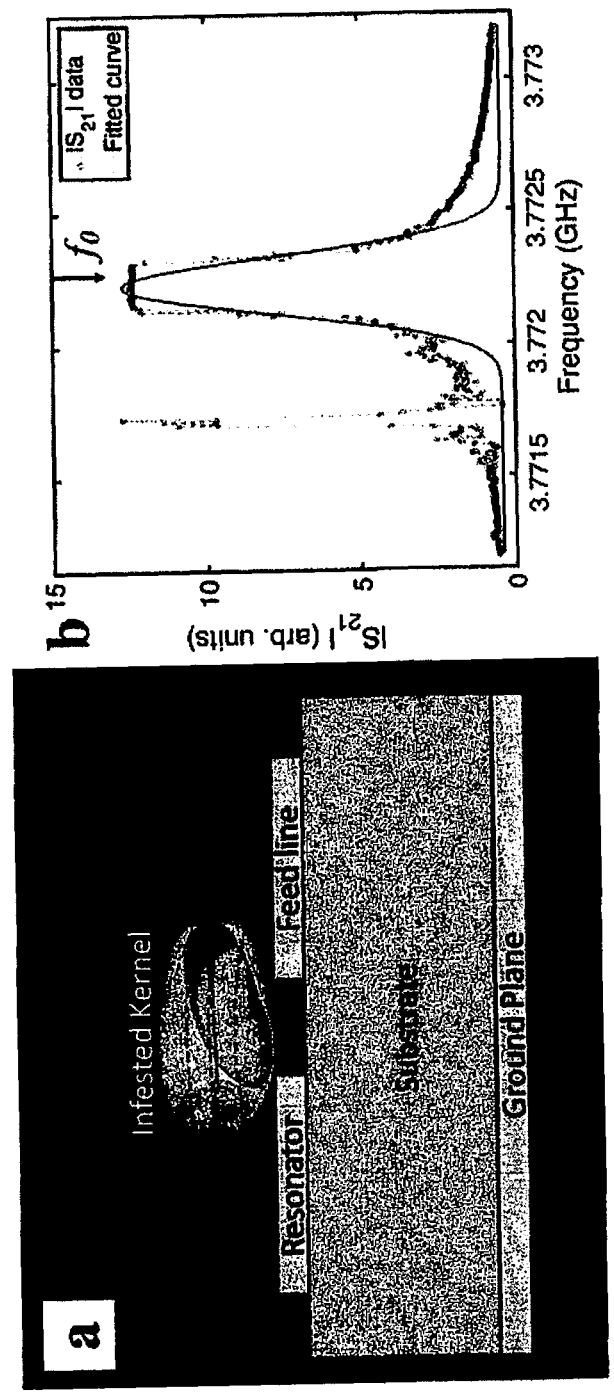
FIG. 6(a) illustrates a grain kernel pest detector using active planar cavity resonator according to another embodiment of the present invention.
FIG. 6(b) shows a graph of the transmission spectrum of the active planar cavity resonator of the grain sample pest detector of FIG. 6(a).

It was found that a lower input power produced a narrower transmission resonance (FIG. 6(b)), but also increased noise. In all measurements, the input microwave power from the VNA to the internal-pest sensor was −50 dBm (0.01 µW). This was achieved with the combination of attenuators both external to and internal to the VNA. 301 evenly spaced frequencies were sampled in the specified band of each measurement and this number was maintained for all measurements. Maintaining a constant sampling number ensured a consistent spectrum sampling rate: in each measurement, the transmission spectrum was recorded 5 times per second (every 0.2 seconds). A consistent sampling rate was required for an accurate analysis, and a sampling rate greater than 2 Hz was necessary to capture the insect movements, which were often observed to occur in time scales shorter than 1-second. Occasionally, insect movements produced spectrum shifts greater than the monitored bandwidth. In these cases, the bandwidth was increased to capture all spectrum shifts. The largest bandwidth monitored in a measurement was 10 MHz; the smallest measurements captured a bandwidth of 2 MHz.

Figure 7A:
FIGS. 7(a) to 7(c) respectively show an X-ray radiograph of a sound (pest-free) wheat kernel, a recorded spectrogram from the grain kernel pest detector in the presence of said sound wheat kernel, and a partial closeup of said spectrogram.
Figure 7B:
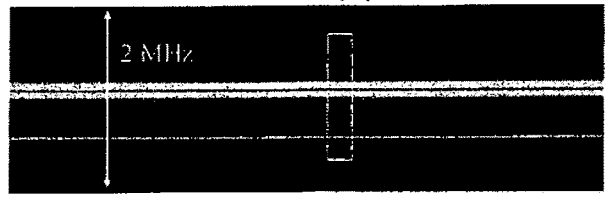
Figure 7C:
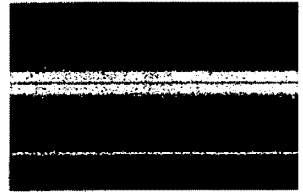
Figure 7D:
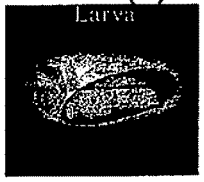
FIGS. 7(d) to 7(f) respectively show an X-ray radiograph of a larva-infested kernel, a recorded spectrogram from the grain kernel pest detector in the presence of said larva-infested kernel, and a partial closeup of said spectrogram.
Figure 7E:
Figure 7F:
Figure 7G:
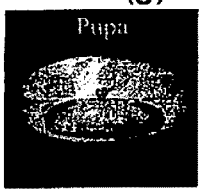
FIGS. 7(g) to 7(i) respectively show an X-ray radiograph of a pupa-infested kernel, a recorded spectrogram from the grain kernel pest detector in the presence of said pupa-infested kernel, and a partial closeup of said spectrogram.
Figure 7H:
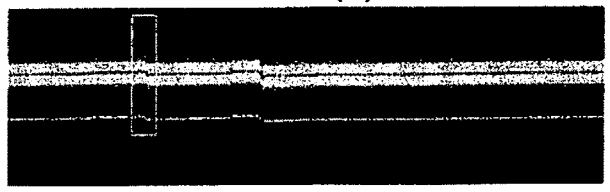
Figure 7I:
Figure 7J:
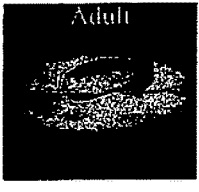
FIGS. 7(j) to 7(l) respectively show an X-ray radiograph of an adult-infested kernel, a recorded spectrogram from the grain kernel pest detector in the presence of said adult-infested kernel, and a partial closeup of said spectrogram.
Figure 7K:
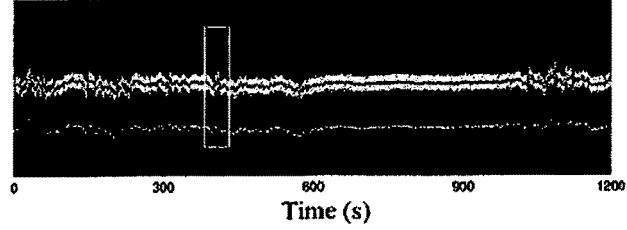
Figure 7L:
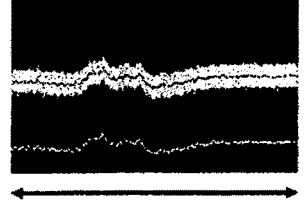

The internal-pest sensor and all power and RF cables were fixed to an optical table to minimize the influence of vibrations on the signal. A kernel support in the form of a dielectric plate with a kernel-shaped slot was fixed flat to the internal-pest sensor to ensure that the individual kernel in each test was placed on the same part of the resonator so that the data reflected variations in insect behaviour instead of variations in the electric field profile of the resonator. For an individual measurement of insect activity, the insect-bearing wheat kernel was placed crease-side down onto the slotted kernel-shaped surface of the dielectric kernel support of the sensor. To block external wireless signals, the internal-pest sensor was shielded with microwave-absorbing material (C-RAM LF-77, Cummings Microwave). The shielding was also opaque to visible light. Observations of kernels bearing *S. oryzae* in the larval, pupal, and adult development stages were performed. As control measurements, measurements were also taken of non-insect-bearing kernels, kernels with dead insects (terminated by freezing), empty kernels from which the adults had previously emerged, and an empty-sensor scenario in which no kernel was placed on the internal-pest sensor. In all control measurements, the result was the same, and a typical spectrogram of such results is shown in FIG. 7(b). All measurements were conducted at a room temperature of about 23° C.

The resonator constituting the internal-pest sensor was made from microstrip transmission line. Microstrip line consists of a flat conductor separated from a ground plane by a dielectric (insulating) layer. The resonator was modelled and simulated using CAD software (CST Studio Suite, Computer Simulation Technology GmbH. The microstrip structure was then milled from a copper clad, double sided, FR-4 grade laminate (Part #106397, LPKF Laser & Electronics) using a computer-controlled circuit board plotter (Protomat S103, LPKF Laser & Electronics). The board substrate and copper cladding had thicknesses of 1.5 mm and 35 µm, respectively. Finally, the electrical components comprising the regenerative element and the external connectors were hand-soldered to the structure to complete the internal-pest sensor. The addition of the regenerative element decreases the width of the transmission resonance by a factor of approximately $10^2$.

The transmission spectrum of the finished resonator is shown in FIG. 6(b). It consists of two peaks. Only the broader, high-frequency peak was stable in both height and width. The narrow, low-frequency peak is a discrete spurious signal, and was unstable. The spurious signal may have been caused by intermodulation products resulting from nonlinearities in the amplifier. In the experimental analysis, examination was made of only the centre of the broad peak, $f_0$. It was found that the spurious signal had little effect on the fitting procedure used to obtain $f_0$ because it's distance from the main peak is large relative to the width of both peaks. As different kernels were placed on the sensor, the steady-state position of $f_0$ would vary between 3.76 GHz and 3.83 GHz, depending on the individual features of each kernel such as the size, shape, and moisture content. The size of the insect and the cavity it created could also affect the steady-state position of $f_0$.

The dielectric support fixture that holds the kernels in place on the resonator during the measurements was modelled using CAD software and cut using the circuit board plotter. It was then fixed to the resonator board with brass screws. Fixing the board to the resonator induced a one-time shift in $f_0$, but did not introduce additional noise.

*Sitophilus oryzae* obtained from colonies maintained in the lab, and originally taken from a flour mill in the province of Manitoba, Canada, were used in this study. The colonies were reared at 30±1° C. and 70±5% relative humidity (rh) at dark. To obtain kernels bearing insects, approximately 1000 adults were introduced to a jar containing 2 kg of rearing medium. The rearing medium was whole hard red spring wheat kernels (14% MC [ASABE, 2009]). The jar was kept at the same rearing conditions as the parent colony for 48 h to allow the adults to lay eggs. The adults were then separated from the rearing medium using a sieve with 1.651 mm apertures. To obtain kernels bearing larvae, pupae, and adults, kernels were retrieved from the jar after 10, 23, and 28 d, respectively. Infestation status was visually examined using a soft X-ray imaging system (MX-20, Faxitron Bioptics, LLC).

To obtain the centre of the transmission resonance, $f_0$, (FIG. 6(*b*)) the MATLAB fit function was used to fit the Gaussian $|S_{21}|=A \exp[-(f-f_0)^2/c^2]+d$ to the recorded spectra, with the independent variable being the frequency, f, and the dependent variable being $|S_{21}|$ (as seen in FIG. 6(*b*)), with A, c, and d corresponding to the peak height, width, and vertical offset, respectively, though these last three variables were not considered in the final analysis. The width, c, was kept constant during fitting. This process consistently extracted the centre of the transmission resonance peak (FIGS. 6(*b*), 7).

On the $f_0$ data, multiple analyses were performed: one to study the variation of measured activity levels, and one focussed on insect detection based on derivative thresholding.

In the analysis of the activity level variation, the first time-derivative of $f_0$, $df_0/dt$, was computed for each measurement. Because the data were discrete samplings of $f_0$, the derivative at time t was approximated numerically as $f'_0(t)=[f_0(t+\Delta t)-f_0(t)]/\Delta t$, where the time step $\Delta t=0.2$ s was constant across all measurements. Then, all $f'_0$ points were combined according to developmental stage and binned into histograms, as shown in FIG. 3. To reduce noise in $f_0$, a 10-point (2 s) moving average filter was applied prior to the analysis. For this analysis, all measurements were truncated to 10 minutes to ensure that each had the same statistical weight.

In the derivative threshold analysis, the detection probability was studied as it varied with the length of observation. This required a quantitative definition of insect activity based on the observed signal. In the absence of any disturbance, the sensor output was relatively constant; occasionally, slow changes in the ambient conditions would cause $f_0$ to drift slowly. In contrast, the sensor response to insect activity was characterized by rapid changes in $f_0$. Therefore, $f'_0$ was looked at as an indicator of activity. Positive detection was therefore defined as instances when the magnitude of $f'_0$ exceeded a prescribed threshold (11.7 kHz/s). The threshold value was selected such that no detections were registered from by the control data (measurements of kernels without live insects). To reduce noise in $f_0$, a 10-point (2 s) moving average filter was applied prior to this analysis.

The next step was to calculate the detection fraction—the fraction of measurements in which an insect was detected—as it varied with observation length and insect stage. First, all measurements were truncated down to a 10-minute window. This measurement window was then divided into equally sized time intervals to simulate short duration observations from among the measurements. All measurements were combined, during which they were grouped by developmental stage (larval, pupal, and adult), and the fraction of the intervals in which $f'_0$ exceeded the defined threshold were counted to estimate the probability of detection. This procedure was repeated for interval widths of 5, 10, 30, 60, 120, 180, 240, 300, and 600 seconds for each stage of *S. oryzae*. The number of individuals tested at each stage were as follows: 73 larvae, 35 pupae, 44 adults, and 70 control measurements (measurements without live insects). This analysis treated the activity of a given individual as a random occurrence in the time scale of the observations.

With reference to FIG. 7, each insect stage was unique not only in its frequencies of activity, but also the signal patterns it created. Adults were the most active and typically showed near-constant activity of varying intensity. With larvae, periods of inactivity punctuated by bursts of activity and short, sudden movements were observed. Pupae were the least likely to be active during measurement. With sound kernels, the spectrum was steady, and the only changes observed were slow thermal drifts in some cases.

The observed activity agrees with existing knowledge of the *S. oryzae* life cycle. To interpret the observed spectrogram patterns in terms of the behaviour inside kernels, reliance was made on an x-ray radiograph study of *S. oryzae* performed by Sharifi and Mills. The known activities of *S. oryzae* larvae include feeding (which simultaneously bores out the cavity), defecating, molting, and resting. Larvae will also construct the pupal chamber in the final 1-2 days before pupation. Regular patterns, such as in FIG. 7(*f*), may reflect a correspondingly regular motion of the larva, such as boring or molting. Pupae, on the other hand, were expected to show little activity: they do not feed, defecate, or molt until eclosion. However, they do still move: by moving their abdomens, pupae sometimes rotate in their chambers, which could explain why signals were still observed in pupae. Adults spend 3-4 days in the kernel waiting for their cuticle to harden before emerging. However, they have several movable appendages: legs, antennae, elytra, and a snout, the movement of which may be the source of the weak but regular and rapid spectrogram patterns as seen in FIG. 7(*k*)-(*l*). Adults will also rotate in the chamber to best align themselves for emergence. Additionally, they will be very active as they begin to emerge.

Figure 8:
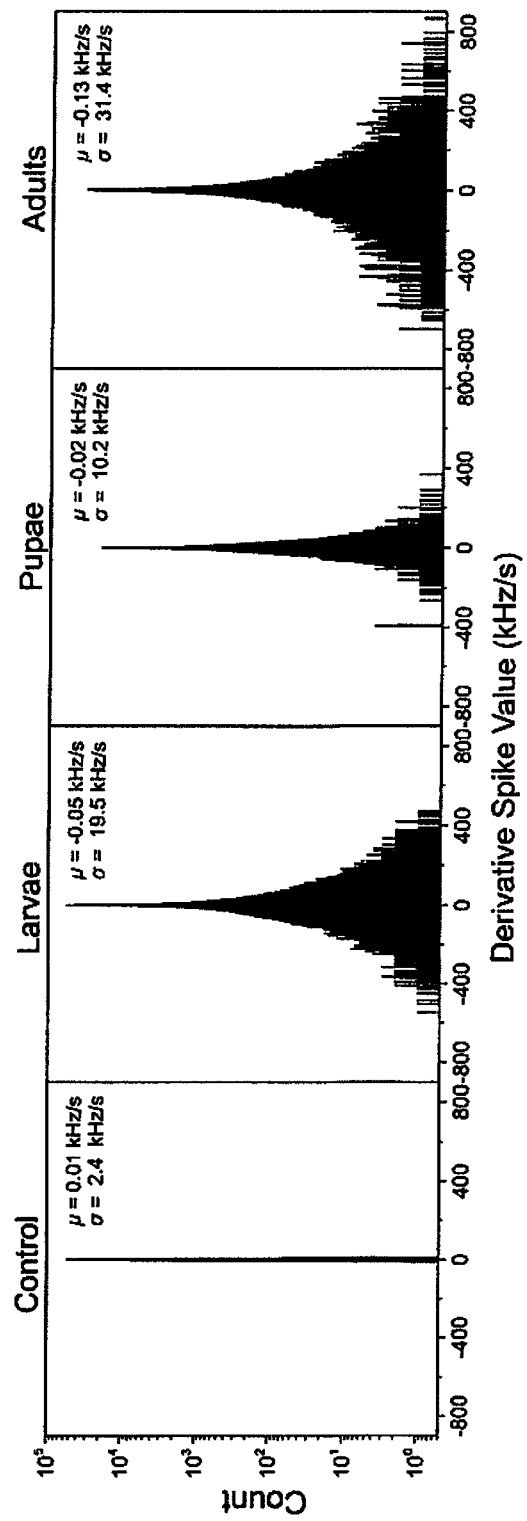
FIG. 8 shows distribution of measured time derivative frequency spikes from the grain kernel pest detector from a control measurement on a sound kernel, and from test measurements on larva, pupa and adult infested kernels.

The examples shown in FIG. 7 are representative of the results, but variations among individuals of the same stage were also observed. FIG. 8 summarizes the variability of approximated first time-derivative of $f_0$, $f'_0$, in the measurements for the insect stages tested. The derivative was approximated by computing the difference between adjacent points and dividing by the time step.

Significant variability was observed in the activity levels of the insects. The test group that showed the least variability was the control group (no live insects inside the kernel). It is seen from FIG. 8 that there is a clear distinction in activity levels measured when insects are present versus the control. Furthermore, there is a markedly lower variability (standard deviation) in $f'_0$ among the control measurements; controls showed a consistently low noise level. The reason for variations in the noise level may be slow drifts caused by changes in the ambient air temperature.

The ability of the sensor to non-intrusively detect insects inside kernels could prove useful for pest-management when screening grain samples. To study this application, the sensor was characterized for binomial (absence-presence) trials of wheat kernels for internal *S. oryzae*, and a study was conducted of how observation duration affected detection probability. This was accomplished by simulating different observation times on the data by dividing the measurement window into smaller time intervals and calculating the fraction of intervals in which activity was detected, as described above. Specifically, the use of the first time derivative of $f_0$, $f_0'$, as an indicator of insect activity was examined.

Figure 9A:
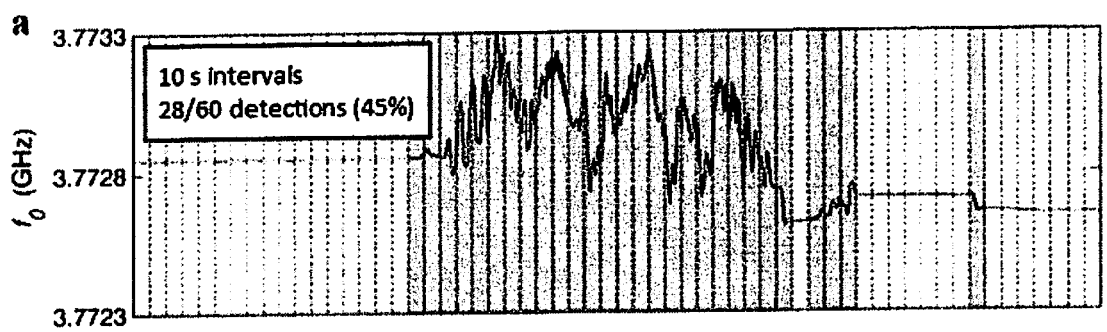
FIG. 9(a) illustrates division of an observed portion of the FIG. 7(e) spectrogram into 10-second intervals, of which those containing a pest-confirming time derivative frequency spike are highlighted.
Figure 9B:
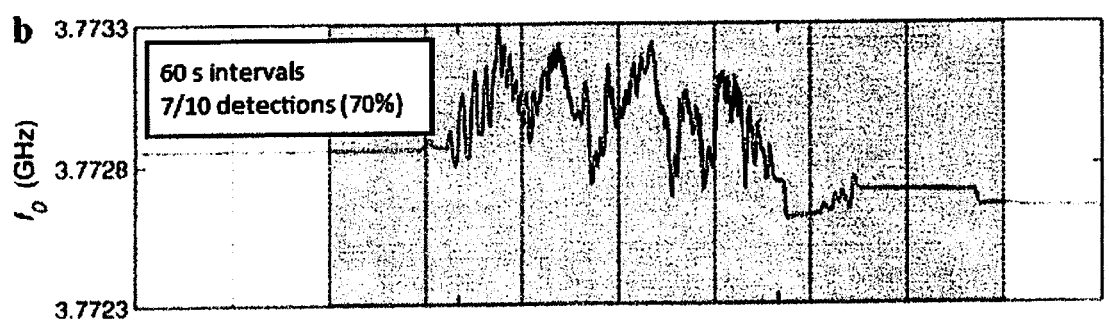
FIG. 9(b) illustrates division of the observed portion of the FIG. 7(e) spectrogram into 60-second intervals, of which those containing a pest-confirming time derivative frequency spike are highlighted.
Figure 9C:
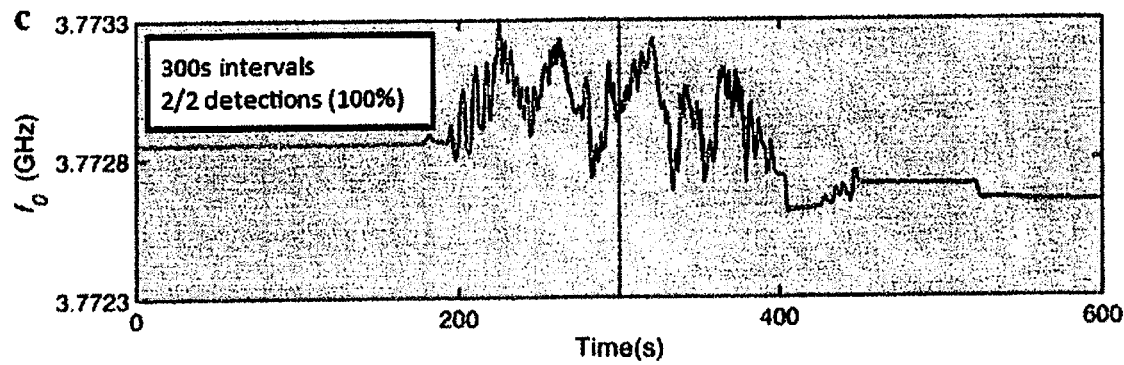
FIG. 9(c) illustrates division of an observed time window from the FIG. 7(e) spectrogram into 300-second intervals, of which those containing a pest-confirming time derivative frequency spike are highlighted.

In this method, detected presence of an internal-pest is counted when intervals have at least one spike in $f_0'$ exceeding a threshold of 11.7 kHz/s, which was selected based on the results shown in FIG. 8. Naturally, longer measurements are more likely to capture spikes in $f_0'$ that exceed the threshold. FIG. 9 illustrates for a single measurement window how the fraction of all intervals in which activity is detected increases with the size of the interval. We see that only intervals having rapid changes in $f_0$ indicate a detection, and that no detections are registered when $f_0$ is steady. This also illustrates the operating principle of the sensor: namely, that detection depends on insect movement.

Figure 10:
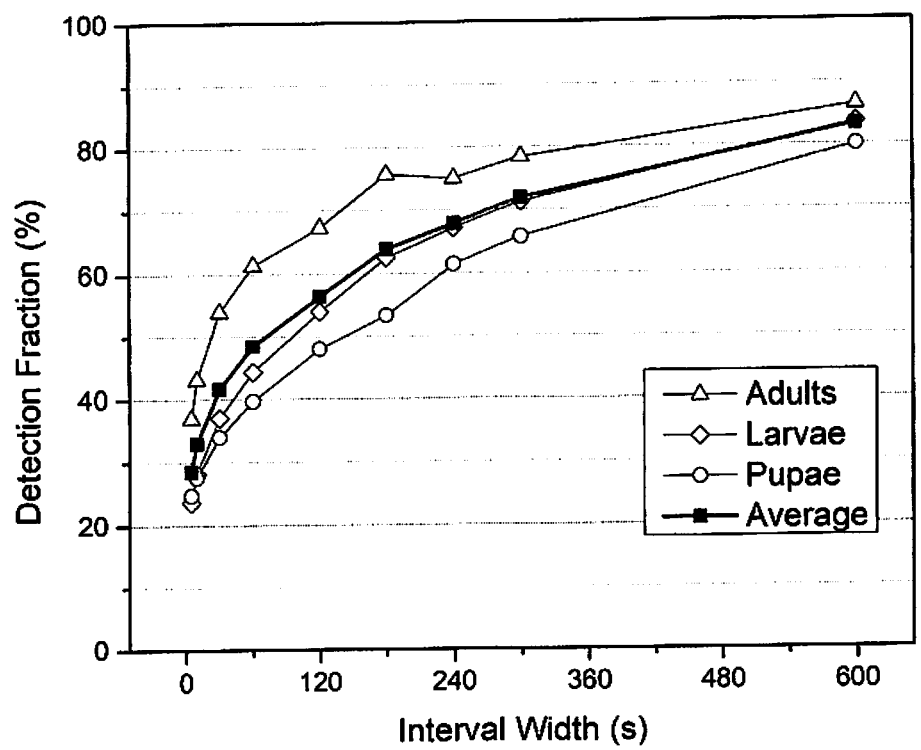
FIG. 10 plots the fraction of time intervals in which pest confirming spikes were found in the observation window, against different interval widths into which said observation window is divisible.

FIG. 10 shows the detection fraction as it varies with interval size and insect type. As expected, the detection fraction increased with the interval width, which simulates observation length. Of the insects detected, it took an average of 2 minutes for a detection to be recorded, and 83% of insects were detected within 10 minutes. For any given interval width, the insect stages in order of highest to lowest detection fraction is generally as follows: adults, larvae, and pupae. This agrees with a qualitative understanding of the behaviour of insects inside kernels, as described above. Quantitatively, the results also follow the expectations suggested by the data in FIG. 8.

In addition to the forgoing embodiment focused on pest detection, another useful application for the sensor is the measurement of grain moisture content. For moisture measurement, grain bulks or samples with differing proportions of moisture content will have correspondingly different permittivities, because water has a very high permittivity at microwave frequencies compared to other materials. In measurement, the electric fields of the sensor are affected by these differences, therefore the moisture content of the grain will be reflected in the output spectrum of the sensor.

One application of the sensor is therefore the continuous monitoring of the moisture content of stored grains. In one embodiment, a plurality of the sensors are embedded in the grain bulk, and their response changes with the moisture content of the grain. The sensors may be carried on cables suspended from the grain bin ceiling so that they are covered by the grain when the bin is filled. As an alternative to in-situ grain bulk moisture measurement in a grain bin or similarly large grain store, another embodiment employs a grain sample moisture measurement system, whether portable, on-site or off-site (e.g. lab-based), that features one or more sensors for measuring smaller samples pulled from grain stores and shipments. This can be used as a quick moisture measurement technique for testing grain shipments at depots and terminals to decide whether to accept or reject such shipments.

Figure 11:
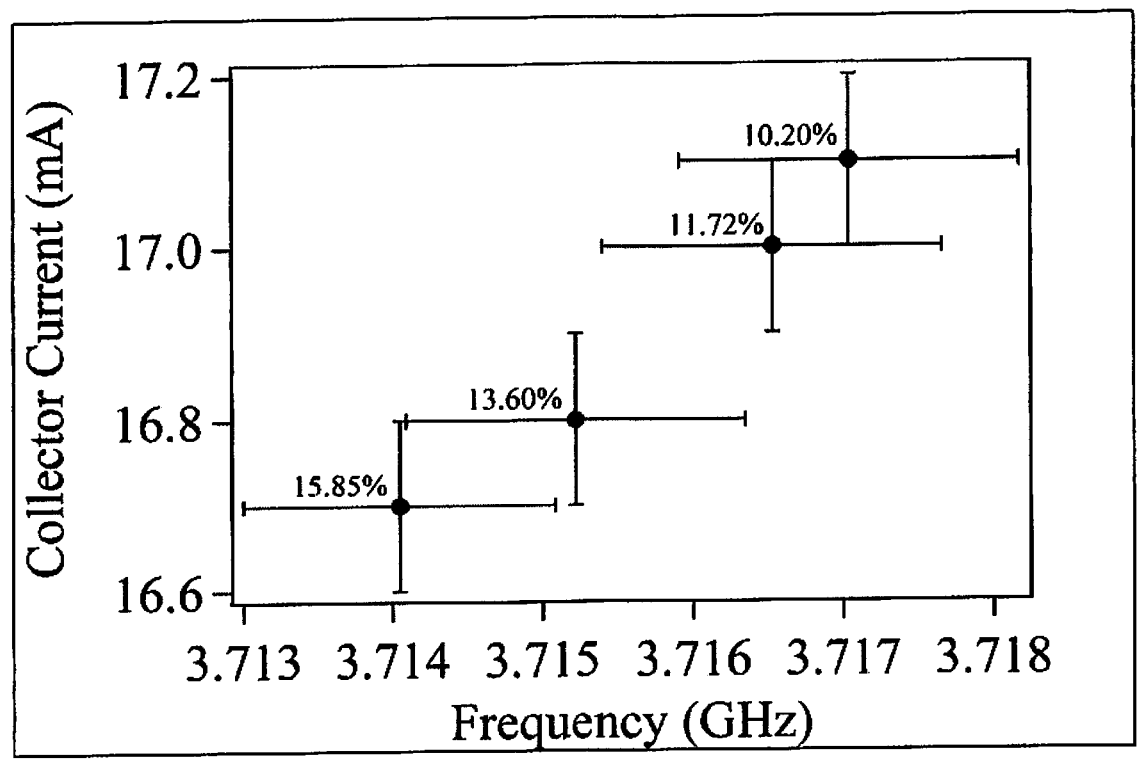
FIG. 11 demonstrates use of an active planar cavity resonator to monitor grain moisture in another embodiment of the present invention, and more specifically plots the results from kernel-based grain moisture measurements.
Figure 12:
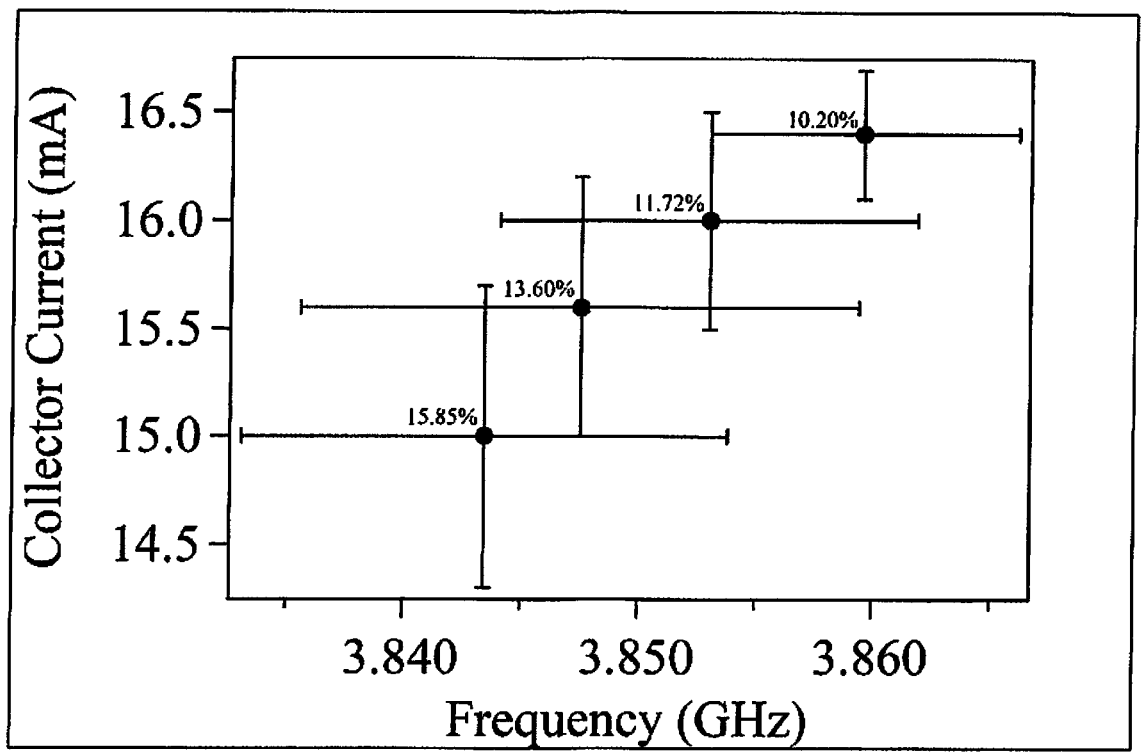
FIG. 12 shows another data plot of the same type as FIG. 11, but from sample-based grain moisture measurements.

In support of such grain moisture embodiments of the present invention, experimentation was conducted on both individual grain kernels, and larger grain samples, the results of which are shown in FIGS. 11 and 12, respectively.

FIG. 11 plots the mean resonating frequency of the active resonator and the collector current drawn by the transistor amplifier in the active resonator when individual kernels of different moisture content levels were placed on the resonator. Measurements were done by affixing the dielectric support to the resonator, placing an individual kernel in each slot, and measuring the frequency and collector current. The measurement was repeated 30 times for each moisture content level, and each measurement was performed with different kernels. Error bars represent the standard deviation of the recorded results. A rough but clear dependence of the collector current and resonance frequency on the moisture content is seen, thereby demonstrating the sensor's ability to monitor moisture content in individual grain kernels.

To confirm extension of the same operating principle to larger grain samples or bulk grain storage, such testing of individual kernels was supplemented by testing on larger volumetric grain samples. The results are shown in FIG. 12, which plots the mean resonating frequency of the active resonator and the collector current drawn by the transistor amplifier in the active resonator when wheat samples of different moisture contents were placed on the resonator. Measurements were done by affixing a container on the resonator and filling it with wheat grain, thus denoting a similar setup to FIG. 5(a). The grain sample was stirred before the frequency and collector current of the resonator were recorded in order to randomize the stacking structure of the grain. This was repeated 30 times for each different moisture content level. Error bars represent the standard deviation of the recorded results. A rough but clear dependence of the collector current and resonance frequency on the grain's moisture content is seen, thereby demonstrating the sensor's ability to monitor moisture content in bulk storage and extracted sample applications.

The results in FIGS. 11 and 12 also demonstrate that the particular resonator operating characteristic that is monitored for detectable shifts representative of changing pest or moisture conditions within the grain need not necessarily be a frequency spectrum of the resonator, and may instead, for example, be the collector current drawn by the transistor amplifier of the active resonator.

Since various modifications can be made in the invention as herein above described, and many apparently widely different embodiments of same made, it is intended that all matter contained in the accompanying specification shall be interpreted as illustrative only and not in a limiting sense.

REFERENCES

Abduljabar, A. A., Porch, A., & Barrow, D. A. (2014). Real-time measurements of size, speed, and dielectric property of liquid segments using a microwave microfluidic sensor. In *Microwave Symposium (IMS), 2014 IEEE MTT-S International* (pp. 1-4). IEEE.

Arlene-Christina, G. D., Jayas, D. S., Fields, P. G., Jian, F., White, N. D. G., & Alagusundaram, K. (2014). Movement of *Cryptolestes ferrugineus* out of wheat kernels and their mortalities under elevated temperatures. *Journal of Stored Products Research*, 59, 292-298.

Boybay, M. S., & Ramahi, O. M. (2012). Material characterization using complementary split-ring resonators. *IEEE Transactions on instrumentation and measurement*, 61, 3039-3046.

Brabec, D., Pearson, T., Flinn, P., & Katzke, D. (2010). Detection of internal insects in wheat using a conductive roller mill and estimation of insect fragments in the resulting flour. *Journal of Stored Products Research*, 46, 180-185.

Drake, V. A., & Reynolds, D. R. (2012). *Radar Entomology: Observing Insect Flight and Migration*. CABI.

Ferrier, G. A., Romanuik, S. F., Thomson, D. J., Bridges, E., & Freeman, M. R. (2009). A microwave interferometric system for simultaneous actuation and detection of single biological cells. *Lab on a Chip*, 9, 3406-3412.

Franks, F. (1972). *Water: A Comprehensive Treatise* volume 1. New York, N.Y., USA: Plenum Press.

Gutiérrez, A., Ruiz, V., Molt'o, E., Tapia, G., & T'ellez, M. (2010). Development of a bioacoustic sensor for the early detection of Red Palm Weevil (*Rhynchophorus ferrugineus* Olivier). *Crop Protection*, 29, 671-676.

Hagstrum, D., Phillips, T., & Cuperus, G. (2012). *Stored Product Protection*. Manhattan, Kans., USA: Kansas State Research and Extension.

Hagstrum, D., & Subramanyam, B. (2006). *Fundamentals of Stored-Product Entomology*. St. Paul, Minn., USA: AACC International.

Jian, F., Doak, S., Jayas, D. S., Fields, P. G., & White, N. D. G. (2016). Comparison of insect detection efficiency by different detection methods. *Journal of Stored Products Research*, 69, 138-142.

Jian, F., Fields, P. G., Hargreaves, K., & Jayas, D. S. (2015). Chill-coma and minimum movement temperatures of stored-product beetles in stored wheat. *Journal of Economic Entomology*, 108, 2471-2478.

Jian, F., Jayas, D., & White, N. (2014a). How many kilograms of grain per sample unit is big enough? part I—comparison of insect detection and density estimation between manual probe sampling and Insector® system. *Journal of Stored Product Research*, 56, 60-66.

Jian, F., Jayas, D. S., & White, N. D. G. (2003). Movement of adult rusty grain beetles, *Cryptolestes ferrugineus* (Coleoptera: Cucujidae), in wheat in response to 5° C./m temperature gradients at cool temperatures. *Journal of Stored Products Research*, 39, 87-101.

Jian, F., Jayas, D. S., & White, N. D. G. (2005). Movement of *Tribolium castaneum* (Coleoptera: Tenebrionidae) adults in response to temperature gradients in vertical and horizontal wheat and corn columns. *Journal of Economic Entomology*, 98, 1413-1419.

Jian, F., Jayas, D. S., White, N. D. G., Fields, P. G., & Howe, N. (2014b). An evaluation of insect expulsion from wheat samples by microwave treatment for disinfestation. *Biosystems Engineering*, 130, 1-12.

Jian, F., Jayas, D. S., White, N. D. G., & Muir, W. E. (2002). Temperature and geotaxis preference by *Cryptolestes ferrugineus* (Coleoptera: Laemophloeidae) adults in response to 5° C./m temperature gradients at optimum and hot temperatures in stored wheat and their mortality at high temperature. *Environmental Entomology*, 31, 816-826.

Jones, A. M., Kelly, J. F., Severtsen, R. H., & McCloy, J. S. (2013). Regenerative feedback resonant circuit to detect transient changes in electromagnetic properties of semi-insulating materials. *Review of Scientific Instruments*, 84, 084703.

Karunakaran, C., Jayas, D., & White, N. (2003). Soft x-ray inspection of wheat kernels infested by *Sitophilus oryzae*. *Transactions of the ASAE*, 46, 739.

Mahroof, R., Subramanyam, B., Throne, J. E., & Menon, A. (2003). Timemortality relationships for *Tribolium castaneum* (Coleoptera: Tenebrionidae) life stages exposed to elevated temperatures. *Journal of Economic Entomology*, 96, 1345-1351.

Mankin, R. W. (2004). Microwave radar detection of stored-product insects. *Journal Economic Entomology*, 97, 1168-1173.

Nick, M. (2011). *New Q-enhanced planar resonators for low phase-noise radio frequency oscillators*. Ph.D. thesis University of Michigan Ann Arbor, Mich., USA.

Nick, M., Member, S., & Mortazawi, A. (2010). Low phase-noise planar oscillators based on low-noise active resonators. *IEEE Transactions on Microwave Theory and Techniques*, 58, 1133-1139.

Pearson, T., & Brabec, D. L. (2007). Detection of wheat kernels with hidden insect infestations with an electrically conductive roller mill. *Applied Engineering in Agriculture*, 23, 639-646.

Rogers (2017). DiClad Series data sheet.

Singh, C. B., Jayas, D. S., Paliwal, J., & White, N. D. G. (2009). Detection of insect-damaged wheat kernels using near-infrared hyperspectral imaging. *Journal of Stored Products Research*, 45, 151-158.

Termatrac (2017). Termatrac website. URL: https://www.termatrac.com.

Yang, Y., Zhang, H., Zhu, J., Wang, G., Tzeng, T.-r., & Xuan, X. (2010). Distinguishing the viability of a single yeast cell with an ultra-sensitive radio frequency sensor. *Lab on a Chip*, 10, 553-555.

Zarifi, M. H., & Daneshmand, M. (2015). Non-contact liquid sensing using high resolution microwave microstrip resonator. In *Microwave Symposium (IMS), 2015 IEEE MTT-S International* (pp. 1-4). IEEE.

The invention claimed is:

1. A method of monitoring grain conditions comprising, with at least one active planar cavity resonator located in proximity with grain to be monitored, monitoring at least one operating characteristic of said active planar cavity resonator for detectable shifts representative of changing conditions within said grain, wherein said active planar cavity resonator comprises a regenerative feedback loop in which there is incorporated a powered amplifier, and said at least one operating characteristic comprises at least one of either a frequency spectrum of the active planar cavity resonator and a collector current drawn by the powered amplifier of said regenerator feedback loop of the active planar cavity resonator.

2. The method of claim 1 wherein said grain is a stored grain bulk, and said at least one active planar cavity resonator is immersed within said stored grain bulk for in-situ monitoring thereof.

3. The method of claim 1 wherein said grain is a sample volume of grain extracted from a larger source of bulk grain.

4. The method of claim 1 wherein said grain is a singular kernel of grain.

5. The method of claim 4 wherein the singular kernel of grain is received on a kernel-shaped support surface of a dielectric support fixed to the activator planar cavity resonator to ensure placement of said kernel in a predetermined position relative thereto.

6. The method of claim 1 wherein the active planar cavity resonator resides in a position exposed to direct contact with said grain.

7. The method of claim 1 wherein said at least one active planar cavity resonator comprises a plurality of active planar cavity resonators at different locations immersed within or dispersed around a volume of grain.

8. The method of claim 1 comprising using a containment structure delimiting boundary walls around the active planar cavity resonator to a contain said grain.

9. The method of claim 1 comprising using said detectable shifts to monitor for presence of insect pests in the grain based detection of at least one of (a) change of an occupancy state of a region of a grain store or sample proximate the resonator from a pest-free state absent any insect pest in said region, to a pest-occupied state in which at least one insect pest is present in said region; (b) movement of at least one insect pest from one location to another within said region of the grain store or sample, thus denoting a change in the position of one or more insect pests within the region; and (c) movement of an internal insect pest inside a grain kernel residing proximate the resonator.

10. The method of claim 9 comprising distinguishing the presence of different insect pest species from one another based on detectable shifts of different magnitude.

11. The method of claim 9 comprising adjusting a temperature of at least part of an environment in which the grain resides to a temperature range in which a targeted insect pest type is known to be active, then monitoring the operating characteristic of said active planar cavity resonator for a detected shift that indicates presence of said one or more targeted insect pest types in said environment.

12. The method of claim 3 comprising using said detectable shifts to monitor for insect presence within the grain, including adjusting a temperature of at least part of said sample volume of grain to a temperature range in which one or more targeted insect pest types are known to be active, then monitoring the operating characteristic of said active planar cavity resonator for a detected shift that indicates presence of said one or more targeted insect pest types in the sample volume of grain.

13. The method of claim 9 wherein the active planar resonator resides on a curved substrate and occupies a curved plane, and is thereby operable to detect a pest from multiple direction faced by said curved plane.

14. The method of claim 1 comprising using said detectable shifts to monitor moisture conditions within the grain.

15. The method of claim 1 wherein monitoring of said at least one operating characteristic comprises monitoring at least said collector current drawn by the powered amplifier.

16. A method of monitoring grain conditions comprising, with an active planar cavity resonator located in proximity with grain to be monitored, monitoring at least one operating characteristic of said active planar cavity resonator for detectable shifts representative of changing conditions within said grain, said method also comprising a reliability test in which temperature conditions in a region at or near the active planar resonator are varied in a controlled manner to switch between different temperature ranges among which pest activity is known to vary, and with a pest intentionally introduced to said region, monitoring the at least one operating characteristic in said different temperature ranges and comparing a difference in magnitudes of detected shifts measured in said different temperature ranges against an expected difference in pest activity within said different temperature ranges.

17. The method of claim 16 comprising performing said reliability test at a location separate and isolated from an environment in which the grain is monitored so that the intentionally introduced pest is prevented accessing said environment.

18. In combination with grain bin for storing bulk grain, at least one sensor placed within or proximate an interior of the grain bin and comprising an active planar cavity resonator of which at least one operating characteristic will undergo a shift in response to changes in conditions in said bulk grain proximate said active planar cavity resonator, wherein said active planar cavity resonator comprises a regenerative feedback loop in which there is incorporated a powered amplifier, and said at least one operating characteristic comprises at least one of either a frequency spectrum of the active planar cavity resonator and a collector current drawn by the powered amplifier of said regenerator feedback loop of the active planar cavity resonator.

19. A grain sample tester comprising a container with an interior space for holding a sample of grain extracted from a larger source of bulk grain, and an active planar cavity resonator situated within or proximate said interior space of the container such that at least one operating characteristic of the active planar cavity resonator will undergo a shift in response to changes in conditions within said sample of grain, wherein said active planar cavity resonator comprises a regenerative feedback loop in which there is incorporated a powered amplifier, and said at least one operating characteristic comprises at least one of either a frequency spectrum of the active planar cavity resonator and a collector current drawn by the powered amplifier of said regenerator feedback loop of the active planar cavity resonator.

20. A sensor comprising an active planar cavity resonator of which at least one operating characteristic will undergo a shift in response to changes in conditions proximate said active planar cavity resonator, wherein said active planar cavity resonator comprises a regenerative feedback loop in which there is incorporated a powered amplifier, said at least one operating characteristic comprises at least one of either a frequency spectrum of the active planar cavity resonator and a collector current drawn by the powered amplifier of said regenerator feedback loop of the active planar cavity resonator, said active planar cavity resonator resides within a curved plane and is thereby operable to detect conditions in multiple directions faced by said curved plane.

21. A grain sample tester comprising an active planar cavity resonator and a dielectric support that is affixed to said active planar cavity resonator and comprises a kernel-shaped support surface configured to receive and hold a singular grain kernel thereon in a predetermined position relative to said active planar cavity resonator to enable detection of conditions within said singular grain kernel through monitoring of at least one operating characteristic of said active planar cavity resonator, wherein said active planar cavity resonator comprises a regenerative feedback loop in which there is incorporated a powered amplifier, and said at least one operating characteristic comprises at least one of either a frequency spectrum of the active planar cavity resonator and a collector current drawn by the powered amplifier of said regenerator feedback loop of the active planar cavity resonator.

* * * * *